US012665072B2

(12) United States Patent
Agarwal et al.

(10) Patent No.: US 12,665,072 B2
(45) Date of Patent: Jun. 23, 2026

(54) COMPUTER-IMPLEMENTED METHOD FOR MAPPING A SCAN PROTOCOL FOR SCANNING A PATIENT TO A STANDARDIZED SCAN PROTOCOL

(71) Applicant: Siemens Healthineers AG, Forchheim (DE)

(72) Inventors: Anuj Agarwal, Tinsukia (IN); Ezhirko S.A, Bangalore (IN)

(73) Assignee: Siemens Healthineers AG, Forchheim (DE)

( * ) Notice: Subject to any disclaimer, the term of this patent is extended or adjusted under 35 U.S.C. 154(b) by 267 days.

(21) Appl. No.: 18/519,381

(22) Filed: Nov. 27, 2023

(65) Prior Publication Data

US 2024/0194327 A1      Jun. 13, 2024

(30) Foreign Application Priority Data

Dec. 7, 2022     (EP) ..................................... 22212018

(51) Int. Cl.
*G16H 30/40*          (2018.01)
*G16H 15/00*          (2018.01)
*G16H 30/20*          (2018.01)

(52) U.S. Cl.
CPC ............. *G16H 30/40* (2018.01); *G16H 15/00* (2018.01); *G16H 30/20* (2018.01)

(58) Field of Classification Search
CPC ........ G16H 30/40; G16H 15/00; G16H 30/20; G16H 50/70; G16H 10/60
See application file for complete search history.

(56) References Cited

U.S. PATENT DOCUMENTS

| | | | | |
|---|---|---|---|---|
| 7,814,025 | B2 * | 10/2010 | Roever | ................ G06Q 20/382 |
| | | | | 705/64 |
| 9,218,584 | B2 * | 12/2015 | Abraham-Fuchs | .......................... |
| | | | | G06Q 30/018 |
| 11,854,705 | B2 * | 12/2023 | Suehling | ................ G16H 10/60 |

(Continued)

OTHER PUBLICATIONS

Hoo-Chang Shin et al.,"Interleaved Text/Image Deep Mining on a Large-Scale Radiology Database for Automated Image Interpretation," Jun. 16, 2016, Journal of Machine Learning Research 17 (2016), pp. 1-24.*

(Continued)

*Primary Examiner* — Omar S Ismail

(57)          ABSTRACT

A computer-implemented method comprises receiving a scan protocol, wherein the scan protocol comprises protocol information pertaining to a set of imaging parameters for imaging a patient; extracting at least one textual protocol parameter from the received scan protocol; generating a combined dataset based on the extracted textual protocol parameters; determining at least one keyword score, the determining the at least one keyword score includes applying a keyword scoring algorithm to the combined dataset to determine the at least one keyword score; determining a selected standardized scan protocol based on the at least one keyword score, the determining the selected standardized scan protocol includes selecting the selected standardized scan protocol out of a plurality of standardized scan protocols; mapping the scan protocol to the selected standardized scan protocol; and providing the mapping of the scan protocol to the selected standardized scan protocol.

12 Claims, 2 Drawing Sheets

(56)                References Cited

U.S. PATENT DOCUMENTS

| | | | | |
|---|---|---|---|---|
| 2002/0029784 | A1* | 3/2002 | Stark | G16H 20/00 |
| | | | | 128/898 |
| 2008/0255782 | A1* | 10/2008 | Bilac | G06Q 50/06 |
| | | | | 340/657 |
| 2013/0311472 | A1* | 11/2013 | Cohen-Solal | G16H 30/20 |
| | | | | 707/737 |
| 2014/0310243 | A1* | 10/2014 | McGee | G06F 16/27 |
| | | | | 707/639 |
| 2017/0124290 | A1* | 5/2017 | Hegde | G16H 30/20 |
| 2018/0026733 | A1* | 1/2018 | Yang | H04N 21/235 |
| | | | | 725/33 |
| 2018/0144822 | A1* | 5/2018 | Guendel | G06N 20/20 |
| 2019/0131011 | A1* | 5/2019 | Sevenster | G06F 16/90324 |
| 2021/0216822 | A1* | 7/2021 | Paik | G10L 15/22 |
| 2022/0028528 | A1* | 1/2022 | Paull | G16H 20/70 |
| 2022/0028529 | A1* | 1/2022 | Paull | G16H 50/20 |
| 2022/0028541 | A1* | 1/2022 | Paull | G16H 20/10 |
| 2022/0399107 | A1* | 12/2022 | Shen | G16H 40/20 |
| 2023/0048700 | A1* | 2/2023 | Sharma | G16H 30/20 |

OTHER PUBLICATIONS

Shohei Fujita et al., "Deep Learning Approach for Generating MRA Images From 3D Quantitative Synthetic MRI Without Additional Scans," Sep. 17, 2019, Investigative Radiology, vol. 55, No. 4, Apr. 2020, pp. 249-253.*

Fakrul Islam Tushar et al., "Classification of Multiple Diseases on Body CT Scans Using Weakly Supervised Deep Learning,"Dec. 1, 2021, Radiology:Artificial Intelligence,2022, pp. 1-8.*

Xin Zhang et al., "Optimizing a machine learning based glioma grading system using multi-parametric MRI histogram and texture features," May 18, 2017, Oncotarget, 2017, vol. 8, No. 29 , pp. 47816-47825.*

Helge C. Kniep et al., "Posterior circulation stroke: machine learning-based detection of early ischemic changes in acute non-contrast CT scans," May 11, 2020, Journal of Neurology (2020) 267, pp. 2632-2639.*

Anne Nielsen et al., "Prediction of Tissue Outcome and Assessment of Treatment Effect in Acute Ischemic Stroke Using Deep Learning," Apr. 6, 2018, stroke, Jun. 2018, pp. 1394-1399.*

Mabotuwana, Thusitha et al: "Mapping Institution-Specific Study Descriptions to RadLex Playbook Entries", Journal of Digital Imaging, vol. 27, No. 3, Jan. 15, 2014 (Jan. 15, 2014), pp. 321-330, XP055193586, ISSN: 0897-1889, 001: 10.1007/610278-013-9663-y.

"RadLex Playbook 2.5 User Guide"; by RSNA Informatics; Version 2.5; Feb. 2018; from http://playbook.radlex.org/playbook/SearchRadlexAction.

* cited by examiner

COMPUTER-IMPLEMENTED METHOD FOR MAPPING A SCAN PROTOCOL FOR SCANNING A PATIENT TO A STANDARDIZED SCAN PROTOCOL

CROSS-REFERENCE TO RELATED APPLICATION (S)

The present application claims priority under 35 U.S.C. § 119 to European Patent Application No. 22212018.0, filed Dec. 7, 2022, the entire contents of which are incorporated herein by reference.

FIELD

One or more example embodiments of the present invention relates to mapping scan protocols, which are usually designated by a user, to standardized protocols, especially according to identifier code dictionary such as the RadLex Playbook IDs (RPIDs) and the RadLex IDs (RIDs) therein.

RELATED ART

The naming, the comprised textual parameters and/or textual description of scan protocols are currently not standardized across different countries or even different institutions. This impedes efforts to compare different types of scan protocols and to establish national or international registries, for example of applied doses.

In the field of radiology, imaging procedures are performed every day to scan the patients for diagnosis. Each of such procedures require precise specifications such as a set of imaging parameters for accurately scanning the patient. In order to use precise specifications, such parameters are documented as a protocol. Scan protocols often comprise textual parameters, e.g., textual descriptions like information about the scan area, focused tissue, organs and/or a clinical intent. Such a documentation, especially in larger institutions is done manually by users (e.g., radiologists). Protocols are usually developed for an individual institution having unique practices and local settings: types of modalities, types of scanner and types of procedure performed i.e., a trauma center does not perform the same procedures as a cancer center. In particular, for larger institutions (e.g., network of hospitals covering a large population area), multiple radiology departments exist and over the years, develop their own protocols, even if they interact frequently. As practice evolves over time, regular updates of these protocols are necessary to maintain efficiency, diagnostic accuracy, and quality of care. The protocols should be consistent throughout a given medical institution. Scanning the patient based on a scan protocol acquires medical images. The medical images are often based on the DICOM standard. The medical images generally comprise the scan protocol, e.g., the medical images comprise tags, wherein the tags comprise a tag description and a tag value. The tag description is for example a label for the tag value, wherein the tag value can be set and/or filled by the user. For example, a medical image and/or a scan protocol comprise as "Scan area" as tag description and "Heart, left chamber" as tag value.

The Radiological Society of North America (RSNA) has developed the so-called RadLex playbook which is a reference for mapping is the effort towards addressing this gap. The RadLex playbook is available at the URL: http://playbook.radlex.org/playbook/SearchRadlexAction currently in its version 2.5 of February 2018. It shall, however, be understood that also later versions of the RadLex playbook are included when the RadLex playbook is mentioned herein.

In the RadLex playbook, each scan protocol (synonym: scan study) is mapped to a standardized identifier code SIC which in this case is termed a "RadLex ID" or "RPID" for short. RPID mapping is useful for standardizing the imaging procedures and/or scan protocols, for comparing similar procedures and studies across several regions and for facilitating including the dose and radiation managements across different institutions. In this way, also false alerts may be reduced in frequency or eliminated entirely. The task of RPID prediction of a scan study (i.e., of mapping the scan study to an RPID) depends on many factors including modality, body region, study description, and much more. Manual mapping of such records occurring in thousands of exams per day is a cumbersome job for the radiologists.

In light of the above, there is a need for a method for mapping scan protocols to standardized scan protocols, wherein the standardized scan protocols, their naming and/or labels are harmonized, such that the scan protocols can be shared and read across different institutions and/or countries. Furthermore, the mapping of the scan protocols needs to be performed in a in a cost-effective, less time-consuming, and consistent way. Moreover, nomenclature and representation of scan protocols representing meaningful information pertaining to clinical intent of the imaging protocol is required.

It is an object of the present invention to provide systems and methods for mapping scan protocols to standardized scan protocols, especially for mapping user created, single and/or multistep scan protocols to standardized protocols, e.g., mapping them to RadLex playbook. This object is provided by the subject-matter of the independent claims.

BRIEF DESCRIPTION OF THE DRAWINGS

The above-mentioned attributes, features, and advantages of this invention and the manner of achieving them, will become more apparent and understandable (clear) with the following description of embodiments of the invention in conjunction with the corresponding drawings. The illustrated embodiments are intended to illustrate, but not limit the invention.

The present invention is further described hereinafter with reference to illustrated embodiments shown in the accompanying drawings, in which:

FIG. 1 illustrates a system for mapping a scan protocol for scanning a patient to a standardized scan protocol;

FIG. 2 illustrates an apparatus for mapping a scan protocol for scanning a patient to a standardized scan protocol;

FIG. 3 illustrates a flowchart depicting steps of a method for mapping a scan protocol for scanning a patient to a standardized scan protocol;

DETAILED DESCRIPTION

Figures 4, 5:
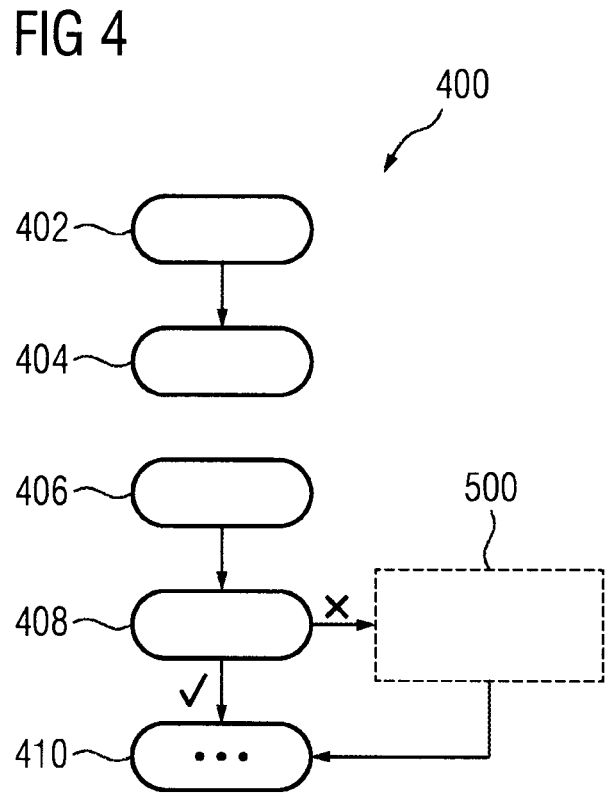
FIG. 4 illustrates a flow chart of another embodiment of the method for mapping a scan protocol.
FIG. 5 illustrates an example of a keyword scoring algorithm.

According to a first aspect, a method for mapping a scan protocol for scanning a patient to a standardized scan protocol is provided. The method comprises the steps:

Receiving a scan protocol, wherein the scan protocol comprises protocol information pertaining to set of imaging parameters for imaging a patient, Extracting at least one textual protocol parameter from the received scan protocol, Generating based on the extracted textual protocol parameters a combined dataset, Determining at least one keyword score, wherein a keyword scoring algorithm is applied to the combined dataset to determine the at least one keyword score, Determining based on the at least one keyword score a selected standardized scan protocol, wherein the selected standardized scan protocol is selected out of a plurality of standardized scan protocols, Mapping the scan protocol to the selected standardized protocol.

The computer implemented method can be implemented and/or executed by a computer, computer system or network and/or by a cloud computing system. The method is for mapping one or more scan protocols to a standardized scan protocol. Mapping means especially finding, relating and/or connecting exactly or at least one standardized scan protocol for/with the scan protocol, wherein the standardized scan protocol is the most related, most similar scan protocol of the standardized scan protocols and/or has the same clinical intent as the scan protocol. The scan protocol is a protocol for imaging, especially medical imaging. For example, the scan protocol is a protocol for magnetic resonance imaging, computed tomography imaging and/or PET imaging. The scan protocol can be based on the DICOM standard. The scan protocol is especially stored as DICOM data and/or the scan protocol is comprised by DICOM data, e.g., comprised by medical image data, wherein the medical image data are based on the DICOM standard. The scan protocol is especially a user defined, user adapted or customized scan protocol.

The scan protocol comprises textual information and preferably numerical information. For example, the scan protocol comprises tags, for example, DICOM tags, tag descriptions and/or tag values. The scan protocol comprises preferably a description of the scan, especially textual information, parameter of the scan, a scan modality, scan area and/or clinical intent. The scan protocol can be in different languages, especially in any official language spoken in the world. The standardized scan protocol is especially harmonized scan protocol. The standardized scan protocol is, for example, in a universal and/or common language, for example, the standardized scan protocol is in English or Latin. Particularly, the standardized scan protocol is based on the RadLex playbook and/or has a RadLex playbook ID.

The step of receiving a scan protocol is for example implemented and/or based on an interface. For example, the scan protocol is provided by a local system, a scanner, database, and/or PACS. The received scan protocol is preferably based on the DICOM standard. The scan protocol comprises protocol information. The protocol information can be related to imaging parameters, also called scanning. The protocol information is especially describing and/or pertaining to settings and parameters of scanning the patient. The protocol information especially comprises textual, numerical, image data and/or information.

In the step of extracting at least one textual protocol parameter. The textual protocol parameter is extracted out of the received scan protocol. The textual protocol parameter is especially a string, one or more words, a sentence, a tag, a tag description, a tag value and/or text.

Based on the extracted textual protocol parameter a combined dataset is generated and/or determined. For example, all extracted textual protocol parameters are combined and/or stacked together as the combined dataset. The combined dataset is especially a string and/or text dataset. The combined dataset can be configured as a text dataset and/or as a vector, wherein the entries of the vector are the extracted textual protocol parameters. The combined dataset comprises the extracted textual protocol parameters and/or is based on them. For example, the combined dataset comprises the extracted textual protocol parameters translated into another language, for example, translated into English and/or a RadLex IDs and/or RadLex terms.

Based on the combined dataset and therefore based on the extracted textual protocol parameters a keyword score is calculated, the determined and/or generated. In particular, a plurality of keyword scores is determined based on the combined dataset. The keyword score is determined by applying keyword scoring algorithm on the combined dataset. The keyword scoring algorithm is, for example, based on machine learning and/or deep learning. Alternatively, and/or additionally, the keyword scoring algorithm can be an analytical term and/or mathematical formula. The keyword score is based on the combined dataset and/or the keyword scoring algorithm is a function which maps the combined dataset to a vector and/or real numbers. The keyword score is, for example, a score which rates how similar the scan protocol is to the standardized scan protocol for. In particular, the keyword score rates how often the textual protocol parameters of the combined dataset are used in the standardized protocol. For example, the keyword scoring algorithm rates and/or scores which standardized scan protocol uses the same textual protocol parameters. For example, the keyword scoring algorithm compares each standardized scan protocol and/or the protocol information's of the standardized scan protocol with the combined dataset, especially the extracted textual protocol parameters of the combined dataset.

Based on the at least one keyword score and/or based on several keyword scores a selected standardized scan protocol is determined and/or a standardized scan protocol is selected out of a plurality of standardized scan protocols. The selection of the standardized scan protocol is based on the keyword score and/or keyword scores. In particular, the standardized scan protocol with the highest keyword score and/or the highest keyword scores for the scan protocol is selected as the selected standardized scan protocol. Especially the standardized scan protocol which has the most similarity and/or same clinical intent based on the protocol information, especially on the textual protocol parameters, is determined. The scan protocol is then mapped to the selected standardized protocol. For example, the scan protocol is connected with the selected standardized protocol and/or the scan protocol is labeled with the selected standardized protocol.

One or more example embodiments of the present invention is based on the idea to provide a method to standardize and/or harmonize scan protocols, which can be built and/or adapted by a user and/or are based on local languages. The computer implemented method uses the textual information of the scan protocol and keyword score to determine the best fitting standardized protocol for the scan protocol. By extracting and using the textual information, instead of using the numeric parameters of the scan protocol and/or analyzing acquired images, the most reliable and useful information are used for mapping a scan protocol to a standardized scan protocol with the same clinical intent. By generating the combined dataset, a faster calculation and/or determination of the keyword score and therefore of the selected standardized protocol can be achieved.

According to a preferred embodiment of the invention the method comprises determining of at least one protocol attribute. The at least one protocol attribute is determined for the received scan protocol. The determination of the protocol attribute is based on the extracted textual protocol parameters. Alternatively, the protocol attribute is determined based on the combined dataset. In particular, for each extracted textual protocol parameter at least one and/or exactly one protocol attribute is determined. The protocol attribute is especially a standardized attribute. Especially, the protocol attribute is an attribute of the RadLex and/or the protocol attribute is a RadLex ID and/or connected to a RadLex attribute. For example, the protocol attribute is determined by mapping the extracted textual protocol parameters to the protocol attribute, best fitting protocol attribute and/or especially mapping them to the RadLex ontology and/or to RadLex ID. In particular, the protocol attribute is determined by translating the textual protocol parameter into another and/or standardized language and/or ontology, for example, translating the textual protocol parameters into English, Latin and/or a RadLex entry. The protocol attribute retains and/or is related to a clinical intent. In other words, the textual protocol parameter is mapped to a protocol attribute which has the same clinical intent.

The protocol attribute is a protocol attribute out of a plurality of protocol attributes. The protocol attributes can be comprised by the RadLex, RadLex Playbook, an ontology and/or a database. The protocol attributes are stored in the first database, for example, on a computer, a cloud and/or a public database. For example, the first database is the RadLex ontology. The first database also comprises standardized scan protocols. The standardized scan protocols are for example protocols and/or entries of the RadLex playbook. The first database for example comprises RadLex IDs, RadLex ontology and/or the RadLex playbook. In particular, each of the standardized scan protocols is associated with at least one protocol attribute. Especially each of the standardized scan protocols comprises at least one, preferably a plurality of, protocol attributes. The comprised protocol attributes of a standardized scan protocols are especially the protocol attribute which describes the clinical intent. Preferably, the standardized scan protocol comprises as the protocol attributes the complex entries and/or RadLex IDs retaining the scanning of the patient. In the step of determining the combined dataset the combined dataset is determined based on the protocol attributes. The protocol attributes, which are determined for the received scan protocol and/or the extracted textual protocol parameters, are combined and/or stacked together as the combined dataset. In other words, the combined dataset comprises the determined protocol attributes for the received scan protocol.

This embodiment is based on the idea to determine for the scan protocol a plurality of protocol attributes, which are standardized, for example, as part of RadLex. By extracting the textual information out of the scan protocol and mapping the extracted textual protocol parameters to the standardized protocol attributes, a combined dataset can be determined which is comprising the most useful information in a standardized form for determining the standardized scan protocol.

Preferably, the step extracting at least one textual protocol parameter comprises extracting a protocol name, an anatomical region, a high-level category description, a scan mode, a scanner model, a protocol customization information and/or a scan time is extracted as extracted textual protocol. This embodiment is based on the idea to use the textual protocol parameter's and/or textual information which comprise the most valuable information for determining a standardized scan protocol as mapping partner for a scan protocol. By choosing this textual protocol parameters the resources of the computer, computer system and/or cloud computing system (CPU, RAM) are very effective and/or economical.

According to a preferred embodiment of the invention, the step of determining at least one keyword score is based on the weighting and/or usage of weights. In other words, the extracted textual protocol parameters and/or the determined protocol attributes are weighted in the step of the determination of the keyword score. For example, the keyword scoring algorithm uses weights to reflect the influence and/or influence of the content on the keyword score. This is based on the idea that some protocol attributes and/or some extracted textual protocol parameters are more useful or effective than others. For example, the extracted textual protocol parameter describing the scanning area has more informational content for selecting a standardized scan protocol with the same clinical intent than an extracted textual protocol parameter describing the name of institution of image acquisition. Especially extracted textual protocol parameters and/or protocol attributes related to a scan region, body region and/or anatomical information are weighted highest and/or used with a bigger weight or weighting factor than other extracted textual protocol parameters and/or protocol attributes.

According to an embodiment of the invention in the step of determining at least one keyword score at least one similarity measure is calculated and/or determined as one of the keyword scores. Especially for determining a plurality of keyword scores, a plurality of similarity measures can be determined. The similarity measure is especially a measure for the similarity between the standardized scan protocol and the scan protocol, especially the similarity of the protocol attributes comprised by the standardized scan protocol and the protocol attributes and/or the extracted textual protocol parameters of the scan protocol and/or combined dataset. The similarity measure is especially related to a comparison, similarity and/or an intersection, textual intersection and/or information intersection of the scan protocol and the standardized scan protocols and/or between the extracted textual parameters and/or protocol attributes of the combined dataset of the scan protocol with the standardized scan protocol. For example, a similarity measure and/or the keyword score is calculated and/or determined for each pair of scan protocol and standardized scan protocol of the plurality of scan protocols in the first database. For example, the similarity measure quantifies the number of protocol attributes of the scan protocol that are also in the standardized protocol. For example, 100% of the protocol attributes of the standardized scan protocol are also in the scan protocol.

Particularly, the step of determining the keyword score comprises determining at least one, especially a plurality of, part scores. The part scores are especially a measure of the similarity between the textual protocol parameters and/or protocol attributes with the standardized protocol with the standardized scan protocols of the first database. For example, different part scores are reflecting the similarity of different subsections of textual protocol parameters and/or protocol attributes with the standardized scan protocol.

Preferably, the step of the determining the selected standardized scan protocol comprises a score sorting of the keyword scores, part scores and/or similarity measures. For example, for each combination of standardized scan protocol and scan protocol, combined dataset, protocol attributes and/or textual information, a plurality of keyword scores, part scores and/or similarity measures are determined, wherein the selection of the selected standardized scan protocol is based on the sorting. For example, the keyword scores are numerical sorted, wherein the standardized scan protocol is selected as the selected scan protocol that has the highest keyword scores and/or the highest keyword score.

According to a preferred embodiment of the invention the method comprises the step of checking the received scan protocol if it is a single step or a multistep protocol. The step of checking is preferably before the step of determining the extracted textual parameters. A multistep protocol is for example a scan protocol that has more than one clinical intent, for example scanning different subsections and/or different organs of the patient. For example, medical images are acquired for a patient in with a scan protocol, wherein the scan protocol comprises MR scanning of the liver and afterwards MR scanning of the heart, wherein such a scan protocol is a two step protocol, since the scan protocol has two different clinical intents (liver, heart). If the step checking the received scan protocol has as the result that it is a multistep protocol, the scan protocol is split into split scan protocols. Especially, the number of splits of the multistep scan protocol is determined, wherein the scan protocol is split into this number of split scan protocols. Especially, the split scan protocols are used as received scan protocols for determining the textual information, combined dataset and/ or determining the selected standardized scan protocol. In other words, the method according to one or more example embodiments of the present invention and/or the mapping of the scan protocol to the standardized scan protocol is executed for each of the split scan protocols.

Preferably, the step of generating the combined dataset comprises checking the extracted textual protocol parameters for spelling mistakes and/or abbreviations. The step of determining the protocol attributes can comprise the step of checking for spelling mistakes and/or abbreviations. Particularly, the extracted textual protocol parameters and/or protocol attributes with spelling mistakes and/or abbreviations are corrected and/or presented to a user to correct them. The generation of the combined dataset and/or determining of the protocol attributes is based and/or carried out on the corrected textual protocol parameters. By checking and correcting the extracted textual protocol parameters and/or the protocol attributes a more reliable keyword scoring and/or similarity measure can be calculated and/or determined.

According to a preferred embodiment of the invention, the step of extracting textual protocol parameters comprises separating the extracted textual protocol parameters with more than one word into single words. The single words and/or the extracted textual protocol parameters are used and/or set as tokens, wherein the tokens are mapped to protocol attributes.

Preferably, the determination of the selected standardized scan protocol is based on additional information. The additional information can comprise a similarity measure for a similarity of images comprised or acquired by the received scan protocol with images of the standardized scan protocol. The additional information can comprise numeric parameters and/or settings of the received scan protocol with the standardized scan protocol. In other words, the determination of the standardized scan protocol that should be mapped to the received scan protocol can use the textual protocol parameters in combination with information regarding the similarity of images and/or numeric parameters and/or settings.

An apparatus for mapping a scan protocol to a standardized scan protocol according to one or more example embodiments of the present invention is provided. The apparatus comprising at least one processing unit, and a memory communicatively coupled to the one or more processing units. The memory comprises a protocol mapping module configured to perform the aforementioned method steps.

A system for mapping a scan protocol to a standardized scan protocol according to one or more example embodiments of the present invention is provided. The system comprises a first database comprising a plurality of standardized scan protocols and an apparatus as mentioned above.

A computer-program product having machine-readable instructions stored therein, which when executed by one or more processing units, cause the processing units to perform a method as described above according to one or more example embodiments of the present invention is provided.

Hereinafter, embodiments for carrying out the present invention are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

Disclosed embodiments provide systems and methods for mapping a scan protocol to a standardized scan protocol. Throughout the present disclosure, the term "scan protocols" as used herein refers to a set of specifications required for performing imaging procedure a patient and/or describing the parameter and/or settings of an medical imaging scan. The term "scan protocol" can also refer to the term "imaging protocol" and/or used as synonyms. Scan protocols contain information that define the imaging procedures and serve as guidelines for imaging practices. The scan protocol can also comprise information, especially textual information, to describe the scanning of the patient, e.g., to describe the region, body region, organ, tissue and/or details of scanning the patient. Examples of such information include a unique name, a modality used (e.g., Computed Tomography (CT), Magnetic Resonance (MR), Nuclear Medicine (NM), X-rays (XR), Ultrasound (US), etc.), body area scanned (e.g., head, chest, etc.), list of clinical indications justifying the use of this specific protocol, list of types of imaging sequences and associated set of parameters, additional comments (e.g., describing the fact that this imaging procedure is a fast acquisition procedure to be used for uncooperative adults or non-sedated children), and patient handling (e.g., preparation, positioning in the scanner, administration of contrast agent, etc.).

Furthermore, the scan protocols define and/or describe the settings used on the imaging equipment to acquire the images and directs the imaging technologist who operates the scanner in how to perform the examination. The protocol as described here will result in an imaging study (also referred as image data) that comprise at least one medical image acquired by scanning the patient based on the scan protocol. The image data and/or imaging study preferably comprises the scan protocol and/or information about the scan protocol. For the purpose of the present disclosure, the term "scan protocols" refer to the imaging protocols that have been customized by the user or clinician for scanning the patient.

Figures 1, 2, 3:
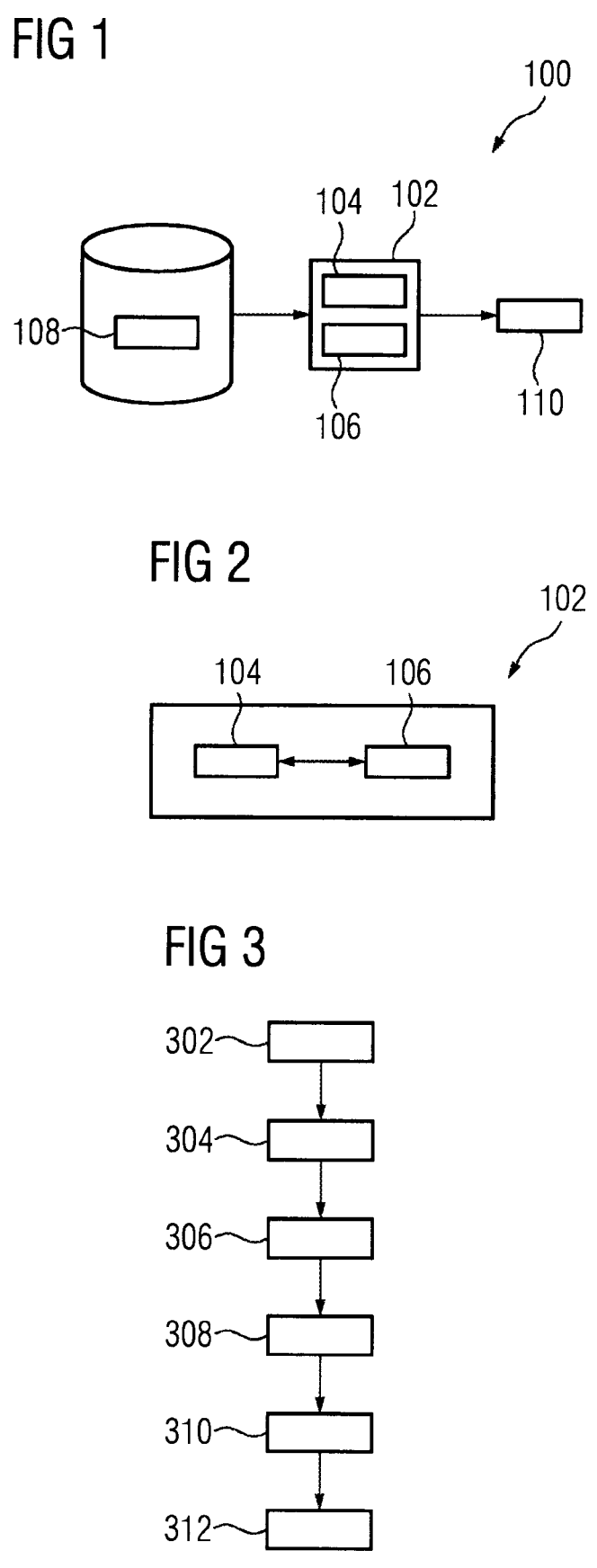

Referring to FIG. 1, a system 100 for mapping a scan protocol for scanning a patient to a standardized scan protocol is described, in accordance with one embodiment of the present invention. The system 100 may be realized as a server-client arrangement or a cloud computing environment. In an exemplary implementation, the system 100 is realized as a server-client arrangement. The system 100 comprises an apparatus 102 which may be a remote server capable of providing cloud-based services such as data storage services, data simulation services, data visualization services, etc. based on the data from one or more user devices 110. The system 100 comprises a processing unit 104, memory 106, a first database 108 and a user device 110. The apparatus 102, the first database 108 and the user device 110 are communicatively coupled to each other. The communication between the apparatus 102, the first database 108, and preferably an user device 110 may be enabled via a communication network (not shown).

In some implementations, the apparatus 102 may be directly or indirectly coupled to communication network. For example, the apparatus 102 may be directly coupled to network via a hardwired network connection. Alternatively, the apparatus 102 may be wirelessly coupled to network via wireless communication channel established between the apparatus 102 and wireless access point (i.e., WAP) which in turn may be directly coupled to network. WAP may be, for example, an IEEE 802.11a, 802.11b, 802.11g, 802.11ac, 802.11ae, Wi-Fi®, RFID, and/or Bluetooth™ (including Bluetooth™ Low Energy) device that is capable of establishing wireless communication channel between user device and WAP. In other examples, the apparatus 102 may be wirelessly coupled to network via wireless communication channel established between the apparatus 102 and cellular network/bridge which may be directly coupled to network. User devices 110 may execute an operating system, examples of which may include but are not limited to, Android®, Apple® iOS®, Mac OS X®; Red Hat Linux®, or a custom operating system.

In some implementations, some or all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example, Bluetooth™ (including Bluetooth™ Low Energy) is a telecommunications industry specification that allows, e.g., mobile phones, computers, smart phones, and other electronic devices to be interconnected using a short-range wireless connection. Other forms of interconnection (e.g., Near Field Communication (NFC)) may also be used.

According to an embodiment, the apparatus 102 comprises the processing unit 104 and the memory 106. Throughout the present disclosure, the term apparatus 102 as used herein refers to a structure and/or module that include programmable and/or non-programmable components configured to store, process and/or share information. Optionally, the apparatus 102 includes any arrangement of physical or virtual computational entities capable of enhancing information to perform various computational tasks. Furthermore, it should be appreciated that the apparatus 102 may be both single hardware server and/or plurality of hardware servers operating in a parallel or distributed architecture. In an example, the apparatus 102 may include components such as memory, a processor, a network adapter and the like, to store, process and/or share information with other computing components, such as user device/user equipment. Optionally, the apparatus 102 is implemented as a computer program that provides various services (such as database service) to other devices, modules or apparatus.

In an embodiment, the system 100 comprises the first database 108 comprising a plurality of standardized scan protocols, especially associated with scan attributes. Additionally, the standardized scan protocols may also be associated with patient specific information. Throughout the present disclosure the term "database" as used in the first database 108 information is stored in the cells of the database 108.

The term "standardized scan protocols" refer in particular to a set of standard specifications required for performing imaging procedure of a patient and/or standard information required to describe the scan protocol, the acquired images and/or clinical intent. The standardized scan protocol preferably comprises standardized descriptions, labels, DICOM tags, information and/or clinical intend. In an example, the standardized scan protocols may be the scan protocols that are considered as a healthcare standard defined by a group or association specializing in radiology. Standardized scan protocols are preferably listed and/or comprised by the RadLex ontology and/or the RadLex Playbook. In another example, the standardized scan protocols may be the scan protocols that are predefined by a manufacturer of an imaging modality (such as a CT scanner). Such standardized scan protocols are by defaults available in the scanner. In particular, the term "standardized scan protocols" refer to to a set of standard specifications required for performing imaging procedure of a patient that have been clustered and associated with imaging identifiers, protocol attributes and/or patient specific information. In an example, the standardized scan protocols represent a clinical intent of the protocol. In another example, the standardized scan protocol may be the scan protocols that have been historically used by the radiologists to perform particular imaging procedures. In another example, the standardized scan protocols may also be the customized imaging protocols that have been determined by the radiologists during an imaging procedure and harmonized to represent clinical intent.

Throughout the present disclosure, the term "imaging identifiers" and/or "protocol attributes" refers to an identifier associated with the scan protocol that represents a clinical intent of the scan protocol. The term "clinical intent" as used herein refers to intent of the scan protocol that is the basis for scanning the patient. Notably, the clinical intent is derived based on various fields available in the standardized scan protocols such as anatomies, purpose of study, scanning technique, and patient information.

It will be appreciated that the standardized scan protocols, imaging identifiers, protocol attributes and/or the association between the standardized scan protocols and corresponding imaging identifiers or protocol attributes are stored in the first database 108. Furthermore, the first database 108 also comprises a plurality of clusters. Herein, each cluster in the plurality of clusters is associated with a standardized scan protocol based on a clinical intent of the information. Notably, the clinical intent is derived based on various fields available in the harmonized imaging protocols such as anatomies, purpose of study, scanning technique, and patient information. Furthermore, the standard imaging protocols may be received from imaging modalities and other data repositories, and then harmonized to represent clinical intent of the imaging protocol. The harmonized protocols are then stored in the first database 108, especially as standardized scan protocols.

The processing unit 104 is configured to receive, by an interface, a scan protocol, wherein the scan protocol comprises information pertaining to set of imaging parameters for imaging/scanning a patient. Further, the processing unit 104 is configured to determine at least one imaging identifier and/or protocol attribute for the received scan protocol based on a clinical intent of the received scan protocol. The processing unit 104 is also configured to extract textual protocol parameter out of the received scan protocol. Furthermore, the processing unit 104 is configured to determine a combined dataset, to determine a keyword score and/or to determine a selected standardized scan protocol and/or to map the received scan protocol to the selected standardized scan protocol.

Referring to FIG. 2, illustrated is an apparatus 102 for mapping a scan protocol to a standardized scan protocol, in accordance with one embodiment of the present invention. The apparatus 102 comprises a processing unit 104 for performing the method steps as aforementioned. The processing unit 104, as used herein, may refer to any type of computational circuit, including, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 104 may also include embedded controllers, such as generic or programmable logic devices or arrays, application specific integrated circuits, single-chip computers, and the like. In general, a processing unit 104 may comprise hardware elements and software elements. The processing unit 104 can be configured for multithreading, i.e., the processing unit 104 may host different calculation processes at the same time, executing them either in parallel or switching between active and passive calculation processes.

The apparatus 102 comprises a memory 106. The memory 106 may comprise a volatile memory and a non-volatile memory. The memory 106 may be coupled for communication with the processing unit 104. The processing unit 104 may execute instructions and/or code stored in the memory 106. A variety of computer-readable storage media may be stored in and accessed from the memory 106. The memory 106 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like.

The memory 106 comprises a protocol mapping module 200 configured to perform the method steps as described in greater detail in FIG. 3. The protocol mapping module 200 is stored in the form of machine-readable instructions on any of the above-mentioned storage media and may be in communication to and executed by the one or more processing units 104.

Referring to FIG. 3, in conjunction with FIGS. 1 and 2, a flowchart depicting steps of a method 300 for mapping a scan protocol to a standardized scan protocol is described, in accordance with one embodiment of the present invention. The method 300 comprises steps 302 to 312 and may be implemented on the system 100.

At step 302, the scan protocol is received, wherein the scan protocol especially comprises information pertaining to a set of imaging parameters for imaging a patient is received. The scan protocol may be received from the user device 110. The scan protocol may be determined based on clinical indications of the patient on whom the scanning is to be performed. The scan protocol may be determined by the radiologist performing the scan. In an example, the scan protocol is determined by the radiologist based on the clinical indications such as one or more symptoms of the patient. In an example, clinical indications for a patient may include symptoms such as "hearing loss in left ear," with the note to perform an "MRI of the head." Within this general examination type, there are many options of clinical scan protocols that are used specifically by the imaging center or radiology department. Examples that are under the general category "MRI of the head" may include "brain tumor," "multiple sclerosis," "angiography," "MR without contrast," "internal auditory canal," "eye-orbit," and so forth. A radiologist reading this order may decide that the order is best fulfilled by using the "internal auditory canal" protocol. Subsequently, the radiologists determine a set of imaging parameters for operating an imaging modality. Non-limiting examples of imaging modality or medical device may be ultrasound imaging device, CT, magnetic resonance imaging (MRI), functional MRI (e.g., fMRI, DCE-MRI, and diffusion MRI), cone beam computed tomography (CBCT), Spiral CT, positron emission tomography (PET), single photon emission computed tomography (SPECT), X-ray, optical tomography, fluorescence imaging, ultrasound imaging, radiotherapy portal imaging and so forth. It will be appreciated that once the scan protocol is determined by the radiologist, the information pertaining to the scan protocol is entered in the user device as input data. In another example, one or more keywords based on clinical indications of the patient such as "MRI of the head", "knee MRI", "angiography" and so forth may also be entered as input data to the user device 110. Subsequently, the one or more keywords and/or scan protocol is received by the processing unit 104 for further processing.

At step 304, at least one textual protocol parameter is extracted and/or determined from the received scan protocol. The at least one textual protocol parameter is preferably determined based on the clinical intent of the received scan protocol. For example, textual protocol parameters related and/or describing the clinical intent of the scan protocol are extracted. The textual protocol parameter comprises, describes and/or is related to a textual, phonetic, spoken language based description of the scan protocol. The textual protocol parameters are in a special embodiment free of numbers and/or comprise only letters. The textual protocol parameters have preferably a string format. For example, the textual protocol parameters comprise DICOM tags, DICOM tag descriptions and/or DICOM tag values of the scan protocol.

At step 306, based on the extracted textual protocol parameters a combined dataset is determined. The combined data set can for example be a combination, list, table, or text comprising the extracted textual protocol parameters.

At step 308, at least one keyword score is determined. The keyword score is determined by applying a keyword scoring algorithm to the combined dataset.

At the step 310, based on the at least one keyword score a selected standardized scan protocol is determined, wherein the selected standardized scan protocol is selected out of a plurality of standardized scan protocols.

At the step 312, the scan protocol, which was received in step 302, is mapped to the selected standardized protocol. The mapping is especially stored, e.g., in the first database, and/or is presented to a user, e.g., presented on a display or monitor.

In an embodiment of the invention at step 310 a plurality of standardized scan protocol are determined based on the at least one keyword score. For example, a number of most fitting standardized scan protocols and/or best mapping partners are determined, e.g., the standardized scan protocols with the highest keyword scores. The determined standardized scan protocols can be presented in a hierarchical manner. It should be noted that the information of the harmonized imaging protocol is arranged in a hierarchical manner and/or sorted based on keyword scores and/or based on a predefined set of rules. The predefined set of rules can be based on anatomy, sub-anatomy, process, study type levels for describing the hierarchy, and so forth.

The keyword score is preferably determined for all or a plurality of combination of the combined data set with all or a plurality of the standardized scan protocols. For example, for each combination of the combined data set and standardized scan protocol a keyword score is determined. Herein, the standardized scan protocols are scan protocols comprised by the RadLex Playbook. The standardized scan protocols comprise textual scan parameters, e.g., a description of the standardized scan protocol, scan attributes and/or parameters.

The generation of the combined data set can comprise techniques such as data cleaning. In an example, the information from the text fields in the received scan protocol, e.g., the extracted textual parameters, are combined as a single string. Additionally, words which do not carry information about the clinical intent of the scan protocol can be removed from the single string. In an example, words not related to anatomical region, body size and protocol name such as the machine name, institute name are removed during data cleaning. Further, the data cleaning and domain specific preprocessing techniques are performed to replace generic words in the scan protocol with RadLex specific words. For example, Angio/Angiogram is replaced with Angiography using the predefined set of rules.

The keyword score is for example a similarity measure and/or based on a similarity measure. In an example, the combined data set is compared against the first database and/or the standardized scan protocols. The similarity measure is preferably based on the Jaccard average similarity or Jaccard similarity index. It should be noted that the Jaccard similarity index compares members for two sets to see which members are shared and which are distinct. The Jaccard similarity index is a measure of similarity for the two sets of data, with a range from 0 to 1. The higher the percentage, the more similar the two datasets which are being mapped with each other. The Jaccard average similarity is given by:

$$J(A, B) = \frac{\#(A \cap B)}{Avg(\#(A), \#(B))}$$

It should be understood that normalizing the similarity index using the average of the string lengths (of A and B) is better when A and B are dissimilar with long length, and wherein #(AUB) reduces the overall similarity index value. It will be appreciated that the calculated value of keyword score determines whether or not the received scan protocol can be accurately associated with a corresponding standardized scan protocol having a similar clinical intent.

In case there is an exact matching based on the combined string, then the mapping score may be 1. Furthermore, if an exact match for the received scan protocol is not found in the RadLex Playbook, then the mapping score may be 0.9, 0.8, 0.7, 0.6, 0.5, 0.4, 0.3 and so forth.

The selected standardized scan protocol can be determined by comparing the keyword score and/or similarity measure with a threshold value to determine whether the keyword score is below the threshold value or above the threshold value. The threshold value may be a numerical value of accuracy of mapping below which the accuracy of mapping is not considered as optimal. In an example, the threshold value may be a value 0.3.

FIG. 4 shows a flow chart of a method for mapping a scan protocol to a standardized scan protocol as another example of the invention. The method is configured to map single and/or multi step scan protocols.

The method for mapping the scan protocol utilizes the textual scan parameters which are generally more indicative of the clinical intent of the study and maps both single-region and multi-region protocols with a single, unified algorithm. The method utilizes the textual information from the scan protocol data and the elements from the RadLex Playbook as tokens and a keyword score, especially a similarity measure. It should be noted that extracted textual parameters concerning the body region and/or anatomy attributes are assigned the highest importance (or weightage) to identify the right clinical intent and/or selected standardized scan protocol.

The method relies on the mapping of tokens using a token mapping dictionary to associated playbook attributes such that protocols with similar intent are clustered within same RadLex ID. It should be understood that if no single RadLex exam can specify the complete clinical intent of a multi-region study, a sub-split rule engine allows for mapping a multi-step multi-region protocol to multiple RadLex exams to utilize the optimal set of Playbook exams.

Developing a token mapping dictionary involves right interpretation of the clinical intent of the study and requires domain knowledge.

A list of extracted textual protocol parameters can be as highlighted in the below table. Out of this, one or more of the following can be used:

TABLE 1

| Textual scan parameters | |
| --- | --- |
| Textual scan parameter | Remarks |
| ProtocolName | Name of the scan protocol |
| AnatomicalRegion | Body region associated to the scan step of the protocol |
| LevelsName | Description of the high-level category for the scan protocol |
| StepsName | Description of actual steps performed during the scan |
| ProtocolStepID | Incremental ID for each step (starts at 0) |
| StepsGroupName | Identifies the type of scan steps (ScanType/ReconType) |
| ScanMode | Mode of scan acquisition |
| CustomProtocol | Identifier for Custom protocols (True/False) |
| BodySize | Identifier of Patient Body Type (Adult/Child) |
| LastUpdated | Datetime: Date and time when the scan was triggered |

The steps of the method 400 for mapping a scan protocol to a standardized scan protocol of FIG. 4 can be configured as following.

At the step 402 the scan protocol, which should be mapped to a standardized scan protocol is received.

In an optional step 404 a conversion into a table or common data format can be applied. For example, a conversion from JSON format to CSV format is utilized. From a module or interface the scan protocol is received in JSON format. Depending on the scanner plugin version, multiple formats of JSON are used in different scanners. In step 404 the scan protocol in JSON formats is converted into a scan protocol in a CSV format.

At the step 406 data cleaning, filtering and extraction is applied to the scan protocol. Out of the various parameters related to a scan performed on the scanner, especially the textual scan parameters according to table 1 are identified to contain the information related to the clinical intent of the study. These textual scan parameters are extracted from the processed CSV and the data values can be validated.

In particular, during the cleaning, the selected data is grouped based on identifier columns ProtocolName, ScannerModel, BodySize, LastUpdated and each group is considered a singular scan protocol. For each group, parameter column AnatomicalRegion and LevelsName are verified to have clean and expected values via a lookup dictionary.

Then, for each group, parameter column StepsGroupName is filtered for the 'ScanType' values and 'ReconType' values are ignored. Within the filtered ScanType steps, subsequent duplicate steps with exactly similar parameter columns LevelsName, AnatomicalRegion, StepsName, ScanMode are ignored.

For a multi-step scan protocol with multiple 'Topogram' scan steps, a sub-split ID is assigned to signify the multiple starts of the scan protocol, if there is a change in the parameter column AnatomicalRegion at the later 'Topogram' scan step. Such scan protocols are considered multi-region and will be assigned multiple RadLex IDs for the combination of steps based on the sub-split ID.

At an optional step 408 the standardized scan protocols are clustered. The standardized scan protocols are well-versed and designed by experts, the clinical intent of the protocols is already understood and can be tagged with an appropriate RadLex Playbook Identifier (RPID) by the expert. For the protocols offered under various Siemens' scanners, a Standard Protocols Master Database has been developed which lists all the known protocols and their associated parameters along with the RadLex ID tag. Especially, step 408 comprises an algorithm to directly lookup the database for any standard protocol identified in the user data.

Any scan protocol not identified in the Standard Protocols Master Database is processed further and a RadLex ID is predicted through the keyword-based algorithm, particularly the keyword scoring algorithm 500.

In a step 410, which can comprise sub steps the identified and/or predicted RadLex ID are associated for the plurality of the scan protocols and/or a RadLex exam description is determined. Any additional information can be utilized to post process the determined standardized scan protocols. The determined standardized scan protocols are presented to the user.

FIG. 5 provides an overview of the keyword scoring algorithm 500.

The method step 502 comprises a data preprocessing and sub-split. From the extracted textual protocol parameters and/or the text of parameter columns ProtocolName & StepsName, words are split into 'tokens' and the list of the tokens are stored in the first database and/or token database. The identified tokens (English or non-English) are verified and mapped to respective Playbook attribute and/or multiple protocol attributes like body region, anatomy, modality, reason, population etc. The abbreviated tokens as well as orthographic, typographic and data errors are corrected and mapped to associated Playbook attribute.

Certain non-English tokens related to attribute pharmaceutical are retained and used as 'keyword tokens'. These 'keyword tokens' are added to a new column 'keywords' in the RadLex Playbook and associated with any related RadLex Exams based on the attribute mapping.

Recognizing the optimal set of multi-region RadLex Exams in Playbook, some of the multi-step protocols cannot be mapped to a single RadLex ID. These scan protocols are split into multiple combination of steps based on parameter columns LevelsName, AnatomicalRegion and StepsName. This novel rule engine allows for a multi-step multi-region protocol to be mapped to multiple RadLex IDs such that the complete clinical intent is properly identified. For a multi-step single-region protocol, no sub-split is performed (unless special case).

As RadLex Playbook is an optimal set of certain combination of playbook attributes, cases may happen where multiple tokens related to various attributes are identified in the protocol steps. For that combination of steps, rules are written to prioritize certain keywords which results in a RadLex ID mapping that suits the clinical intent of the study. Additionally, rules are written to form new 'keyword tokens' with better contextual meaning after combining multiple 'keyword tokens' retained in the multi-token translator step. The new 'keyword tokens' are also appended to the column 'keywords' in the Playbook.

The extracted textual protocol parameters and/or text-based parameter columns ProtocolName, LevelsName, AnatomicalRegion, BodySize, StepsName are joined (or combined) together to form the combined data set, which is a string. It is quite straight-forward for the single-step protocols. For multi-step protocols, a combined string is formed for the specific split scan protocols generated at the multi-step protocol sub-split step.

The step 502 may comprise sub steps 502*a* and 502*b*. In 502*a*, the extracted keyword and/or token are stored in and/or retrieved from the database, e.g., token db. In 502*b*, the information from the standardized scan protocols and/or any domain knowledge for the scan protocol and/or the combined data set is determined and stored in and/or retrieved from the first database. The sub steps are performed as and when necessary.

The method step 504 comprises a keyword scoring mechanism. Based on the plurality of the combined data set multiple token similarity measures are calculated with respect to the Playbook attributes for each of the Radlex Exams.

A similarity measure namely, part score based on the Jaccard similarity index and/or textual intersection is determined. The part score formula is expressed as:

$$\text{part}(A, B) = \frac{(\#(A \cap B))^2}{\#(B)}$$

It should be noted that the part score compares the members for two sets, combined data set A and attribute set B to see which members are shared i.e., the number of intersecting words is determined. Squaring the number of intersecting words in the numerator pushes the score higher for a high number of matches. It should be understood that normalizing the score using the length of the attribute set B returns a whole number for a full match and/or intersection, and for a partial match and/or intersection, a fraction is returned. It should be appreciated that the calculated part score is not dependent of the length of the combined data set A. The part score formula is utilized to determine and/or calculate a plurality of scores with respect to the various protocol attributes as identified from the RadLex Playbook.

For the combined set of Playbook attributes Body_Region and Anatomic_Focus B identified in the RadLex Playbook for the plurality of the RadLex protocols, bp_total_score is calculated for the plurality of the combined data set A as per the part score formula described above.

For the combined set of Playbook attribute Modality B identified in the RadLex Playbook for the plurality of the RadLex protocols, modality_score is calculated for the plurality of the combined data set A as per the part score formula described above.

For the combined set of Playbook attribute Reason B identified in the RadLex Playbook for the plurality of the RadLex protocols, reason_score is calculated for the plurality of the combined data set A as per the part score formula described above.

For the combined set of Playbook attribute Population B identified in the RadLex Playbook for the plurality of the RadLex protocols, population_score is calculated for the plurality of the combined data set A as per the part score formula described above.

Another similarity measure namely, similarity score based on the Jaccard similarity index and/or textual intersection is determined. The similarity score formula is expressed as:

$$similarity(A, B) = \frac{\#(A \cap B)}{Avg(\#(A), \#(B))}$$

It should be noted that the Jaccard similarity index compares members for two sets to see which members are shared and which are distinct i.e., the number of intersecting words is determined. It should be understood that normalizing the similarity index using the average of the string lengths (of A and B) is better when A and B are dissimilar with long length. It should be understood that the calculated similarity score is dependent of the length of the combined data set A so, this requires the combined data set to be pre-processed to remove duplicates tokens and/or tokens which are non-contributing to the clinical intent of the study to suppress any skewness in the similarity score.

The similarity score formula is utilized to determine and/or calculate a sim_score with respect to the combined data set A and the Automated_Long_Name B identified in the RadLex Playbook for the plurality of the RadLex protocols.

Another similarity measure namely, keyword score based on the Jaccard similarity index and/or textual intersection is determined. The keyword score formula is expressed as:

$$keyword(A, B) = \frac{\#(A \cap B)}{\#(A)}$$

It should be noted that the Jaccard similarity index compares members for two sets to see which members are shared and which are distinct i.e., the number of intersecting words is determined. It should be understood that normalizing the score using the length of the non-intersected tokens A in the combined data set after similarity score calculation is better when A and B are dissimilar with long length. This requires the combined data set to be pre-processed to remove duplicates tokens and/or tokens which are non-contributing to the clinical intent of the study to suppress any skewness in the similarity score.

The keyword score formula is utilized to determine and/or calculate a keyword_score with respect to non-intersected tokens remaining after similarity score calculation A and the set of tokens in 'keywords' column B identified in the RadLex Playbook for the plurality of the RadLex protocols.

After all calculations of the individual scores, different combinations of scores are formed based on the Playbook attributes which are associated with the clinical intent of the study. The various combined scores and their priorities are as follows:

bp_total_score, body region and anatomy are assigned the highest importance and/or weightage match_score is a combination and/or summation of modality_score, reason_score, keyword_score. Modality, reason for scan and pharmaceutical are assigned the second highest importance and/or weightage final_score is a combination and/or summation of all calculated scores, namely bp_total_score, match_score, sim_score, population_score. This is set as the final level of importance and/or weightage.

Based on the defined priority of the scores, the RadLex IDs are sorted in the step 506, firstly on the bp_total_score, secondly on the match_score and finally on the final_score.

The RadLex ID with the highest score out of the plurality of the RadLex protocols is selected as the final RPID label for the given combined data set.

Special Cases:

Case I: In case, multiple RadLex IDs somehow get exactly equal scores, verify that the Body Region and Anatomy are different and select the first RadLex ID.

In case, Body region and Anatomy are also exactly similar, then generally the issue is with the pharmaceutical attribute of the mapped RPID. To resolve these cases, if the combined string does not contain keywords related to contrast, then assuming the study is non-contrast, the scores are re-calculated after appending 'without' to the combined string. Finally, the RadLex ID with the highest score is now selected as the final RPID label for the given combined string.

Case II: For certain CT scan protocols, the selected RadLex ID may be less suited or relevant with respect to the clinical intent of the study due to various reasons and/or certain Playbook attribute are likely to be missing from the selected RadLex ID. In such cases, the final score would lie below a certain threshold, which can be a single value for the final score and/or multiple thresholds for the plurality of the similarity scores.

To resolve such mismatches, RadLex Playbook attribute values are extracted from the combined textual information of the scan protocol and are combined in an ordered fashion like how the Automated_Long_Name is constructed for a RadLex standardized scan protocol. This generated Custom Tag would be much more suited to correctly define the clinical intent of the study.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The expression "a number of" means "at least one". The mention of a "unit" or a "device" does not preclude the use of more than one unit or device. The expression "a number of" has to be understood as "at least one".

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "display-ing" or the like, refer to the action and processes of a computer system, or similar electronic computing device/ hardware, that manipulates and transforms data represented as physical, electronic quantities within the computer sys-tem's registers and memories into other data similarly represented as physical quantities within the computer sys-tem memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hard-ware.

The module may include one or more interface circuits. In some examples, the interface circuits may include wired or wireless interfaces that are connected to a local area network (LAN), the Internet, a wide area network (WAN), or com-binations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being inter-preted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

According to one or more example embodiments, com-puter processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer process-ing devices may perform the operations and/or functions of the various functional units without sub-dividing the opera-tions and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a per-manent mass storage device (such as a disk drive), solid state (e.g., NAND flash) device, and/or any other like data storage mechanism capable of storing and recording data. The one or more storage devices may be configured to store com-puter programs, program code, instructions, or some com-bination thereof, for one or more operating systems and/or for implementing the example embodiments described herein. The computer programs, program code, instructions, or some combination thereof, may also be loaded from a separate computer readable storage medium into the one or more storage devices and/or one or more computer process-ing devices using a drive mechanism. Such separate com-puter readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

Computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

Shared memory hardware encompasses a single memory device that stores some or all code from multiple modules. Group memory hardware encompasses a memory device that, in combination with other memory devices, stores some or all code from one or more modules.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Wherever meaningful, individual embodiments or their individual aspects and features can be combined or exchanged with one another without limiting or widening the scope of the present invention. Advantages which are described with respect to embodiments of the present invention are, wherever applicable, also advantageous to other embodiments of the present invention.

The invention claimed is:

1. A computer-implemented method, the method comprising:
   receiving a scan protocol, wherein the scan protocol comprises protocol information pertaining to a set of imaging parameters for imaging a patient;

extracting at least one textual protocol parameter from the received scan protocol;
   generating a combined dataset based on the extracted textual protocol parameters;
   determining at least one keyword score, the determining the at least one keyword score includes applying a keyword scoring algorithm to the combined dataset to determine the at least one keyword score;
   determining a selected standardized scan protocol based on the at least one keyword score, the determining the selected standardized scan protocol includes selecting the selected standardized scan protocol of a plurality of standardized scan protocols;
   mapping the scan protocol to the selected standardized scan protocol;
   providing the mapping of the scan protocol to the selected standardized scan protocol; and
   determining at least one protocol attribute for the received scan protocol based on the at least one extracted textual protocol parameter, wherein,
      the at least one determined protocol attribute pertains to a clinical intent of the received scan protocol,
      the at least one determined protocol attribute is one of a plurality of protocol attributes which are stored in a first database,
      the first database comprises the plurality of standardized scan protocols, each of the standardized scan protocols is associated with at least one of the plurality of protocol attributes, the plurality of protocol attributes represent a clinical intent of the associated standardized scan protocol, and
      the generating generates the combined dataset based on the determined at least one protocol attribute.

2. The method of claim 1, wherein the extracting extracts at least one of a protocol name, an anatomical region, a high-level category description, a scan mode, a scanner model, a protocol customization information or a scan time as the extracted textual protocol parameter.

3. The method of claim 1, wherein the determining the at least one keyword score is based on a weighting of at least one of the extracted textual protocol parameters or the protocol attributes, wherein at least one of extracted textual protocol parameters or protocol attributes pertaining to at least one of a body region or anatomical information are weighted highest.

4. The method of claim 1, wherein the determining at least one keyword score determines a similarity measure as at least one of the keyword scores based on at least one of the combined dataset or the first database.

5. The method of claim 4, the determining the at least one keyword score determines a part score as a similarity measure based on a textual intersection between the combined dataset and standardized scan protocols of the first database.

6. The method of claim 4, wherein the determining the selected standardized scan protocol comprises a score sorting of at least one of the keyword score or the similarity measure, wherein the standardized scan protocol related to a highest keyword score or similarity measure is selected as the standardized scan protocol.

7. The method of claim 1, further comprising:
   determining if the received scan protocol is a single step or a multistep scan protocol, wherein the received scan protocol is split into split scan protocols if the received scan protocol is a multistep multiregion scan protocol, and the extracting at least one textual protocol parameter is based on the split scan protocols.

8. The method of claim 1, wherein the generating the combined dataset comprises, checking at least one of the extracted textual protocol parameters or the protocol attributes for at least one of spelling mistakes or abbreviations, wherein the at least one of the spelling mistakes or the abbreviations are corrected in the at least one of the extracted textual protocol parameters or the protocol attributes.

9. An apparatus for mapping a scan protocol to a standardized scan protocol, the apparatus comprising:

at least one processing unit; and a memory communicatively coupled to the at least one processing unit, the memory comprising a protocol mapping module configured to cause the apparatus to perform the method of claim 1 when executed by the at least one processing unit.

10. A system for mapping a scan protocol to a standardized scan protocol, the system comprising:

a first database comprising a plurality of standardized scan protocols; and the apparatus of claim 9.

11. A computer program product comprising machine readable instructions, that when executed by a processing unit of a system, cause the system to perform the method of claim 1.

12. The method of claim 1, wherein the extracting extracts at least one of a protocol name, an anatomical region, a high-level category description, a scan mode, a scanner model, a protocol customization information or a scan time as the extracted textual protocol parameter.

\* \* \* \* \*